(12) United States Patent
Bartlett

(10) Patent No.: US 6,843,799 B2
(45) Date of Patent: Jan. 18, 2005

(54) SUTURE ANCHOR SYSTEM AND ASSOCIATED METHOD

(76) Inventor: Edwin C. Bartlett, 609 Bremerton Dr., Greenville, NC (US) 27858

(*) Notice: Subject to any disclaimer, the term of this patent is extended or adjusted under 35 U.S.C. 154(b) by 55 days.

(21) Appl. No.: 10/105,807

(22) Filed: Mar. 25, 2002

(65) Prior Publication Data
US 2003/0181946 A1 Sep. 25, 2003

(51) Int. Cl.$^7$ .............................................. A61B 17/04
(52) U.S. Cl. ....................................................... 606/232
(58) Field of Search ............................ 606/232, 60, 72, 606/73, 75, 104

(56) References Cited

U.S. PATENT DOCUMENTS

| | | |
|---|---|---|
| 4,669,473 A | 6/1987 | Richards et al. |
| 4,946,468 A | 8/1990 | Li |
| 5,085,661 A | 2/1992 | Moss |
| 5,102,421 A | 4/1992 | Anspach, Jr. |
| 5,203,787 A | 4/1993 | Noblitt et al. |
| 5,207,679 A | 5/1993 | Li |
| 5,258,016 A | 11/1993 | DiPoto et al. |
| 5,269,809 A | 12/1993 | Hayhurst et al. |
| 5,354,298 A | 10/1994 | Lee et al. |
| 5,405,359 A | 4/1995 | Pierce |
| 5,423,860 A | 6/1995 | Lizardi et al. |
| 5,464,425 A | 11/1995 | Skiba |
| 5,522,844 A | 6/1996 | Johnson |
| 5,540,718 A | 7/1996 | Bartlett |
| 5,584,835 A | 12/1996 | Greenfield |
| 5,626,612 A | 5/1997 | Bartlett |
| 5,626,613 A | 5/1997 | Schmieding |
| 5,647,874 A | 7/1997 | Hayhurst |
| 5,683,401 A | 11/1997 | Schmieding |
| 5,683,418 A | 11/1997 | Luscombe et al. |
| 5,709,708 A | 1/1998 | Thai |
| 5,782,862 A | 7/1998 | Bonutti |
| 5,782,863 A | 7/1998 | Bartlett |
| 5,814,051 A | 9/1998 | Wenstrom |
| 5,814,070 A | 9/1998 | Borzone et al. |
| 5,814,071 A | 9/1998 | McDevitt et al. |
| 5,814,072 A | 9/1998 | Bonutti |
| 5,814,073 A | 9/1998 | Bonutti |
| 5,868,789 A | 2/1999 | Huebner |
| 5,871,503 A | 2/1999 | Bartlett |
| 5,879,372 A | 3/1999 | Bartlett |
| 5,961,538 A | 10/1999 | Pedlick et al. |
| 6,146,408 A | 11/2000 | Bartlett |
| 6,306,158 B1 | 10/2001 | Bartlett |

FOREIGN PATENT DOCUMENTS

| | | |
|---|---|---|
| WO | WO 95/08295 | 3/1995 |
| WO | WO 97/37595 | 10/1997 |

Primary Examiner—Michael Milano
Assistant Examiner—D. Jacob Davis
(74) Attorney, Agent, or Firm—Alston & Bird LLP

(57) ABSTRACT

A suture anchor system configured so as to facilitate implantation of a suture anchor within a bore formed in a bone, so as to secure a suture to the bone, is provided. Such a system comprises a suture anchor having a suture operably engaged therewith and an insertion tool having a tip and defining a first axis. The insertion tool is discrete with respect to the suture anchor and is capable of implanting the suture anchor within the bore such that the suture anchor is secured in the bone. The tip is engagable with the suture anchor and is configured to cooperate therewith so as to prevent the suture anchor from rotating about the first axis. Further, the insertion tool is configured with respect to the suture anchor such that a rotational force exerted on the insertion tool rotates the suture anchor about a second axis disposed perpendicularly with respect to the first axis. A predetermined axial seating force is then applied to the insertion tool, outwardly of the bore, to seat the suture anchor in the bore. The insertion tool is further configured so as to require an axial separation force to be applied thereto so as to separate the insertion tool from the suture anchor, wherein the separation force is no less than the seating force. Associated systems and methods are also provided.

27 Claims, 14 Drawing Sheets

SUTURE ANCHOR SYSTEM AND ASSOCIATED METHOD

BACKGROUND OF THE INVENTION

The present invention relates to a suture anchor for securing a suture to a bone and, more particularly, to a suture anchor system configured so as to allow an axial seating force to be applied to an insertion tool engaged with a suture anchor, so as to seat the suture anchor within a bore in the bone, before the insertion tool can be separated from the suture anchor by the exertion of an axial separation force no less than the seating force.

Suture anchors are known in the art as providing a convenient and effective mechanism for securing bodily tissue to an adjacent bone structure in a human body such as, for example, where a ruptured tendon must be reattached to the corresponding bone. The suture anchor is generally inserted into a bore formed in the bone so as to provide an attachment point for securing a suture to the bone, wherein the suture is then used to secure the adjacent bodily tissue to the bone. Of the many types and forms of suture anchors, the wedge-type suture anchor has shown good promise in practical applications. Examples of such wedge-type suture anchors may be found in U.S. Pat. Nos. 5,540,718, 5,626,612, 5,782,863, 5,871,503, 5,879,372, 6,146,408, and 6,306,158 to Bartlett. U.S. Pat. No. 5,683,418 to Luscombe et al. and U.S. Pat. No. 5,961,538 to Pedlick et al., both assigned to Mitek Surgical Products, Inc., also disclose such wedge-type suture anchors. Thus, U.S. Pat. Nos. 5,540,718, 5,626,612, 5,782,863, 5,871,503, 5,879,372, 6,146,408, and 6,306,158 to Bartlett, U.S. Pat. No. 5,683,418 to Luscombe et al., and U.S. Pat. No. 5,961,538 to Pedlick et al. are incorporated in their entirety herein by reference.

Generally, in practice, a wedge-type anchor having an engaged suture is first engaged with an insertion tool and introduced into a bore drilled into the bone at a location on the bone where the bodily tissue must be affixed. The suture anchor generally includes a first gripping portion, such as a sharp edge or a point, and is designed to rotate as it enters the bore or is in the process of being withdrawn therefrom. As the suture anchor rotates, the first gripping portion bites or penetrates the wall of the bore and causes further rotation of the anchor. At the opposite end of the suture anchor, a second gripping portion is typically provided. The second gripping portion penetrates into the wall of the bore generally opposite the first gripping portion as the suture anchor is rotated, thereby wedging the suture anchor within the bore. When the suture anchor has rotated about the first gripping portion, as much as the second gripping portion will allow with respect to the bone structure surrounding the bore, the suture anchor is in a seated position where it is anchored in the bore and ready to have adjacent bodily tissue attached thereto.

However, while suture anchors are theoretically designed to work with all bones, the structure of bone can vary greatly depending on the area of the body in which the suture anchor is required. Bones generally include a number of trabeculae disposed throughout. The spacing of the trabeculae within the intermedulary canal of the bone is often a good indicator of the density of the bone. Cortical bone is solid bone without visible interstitial spaces and is typical of the midshafts, or diaphyseal regions, of long bones. Metaphyseal and epiphyseal bone, which is the bone around the joints at the opposing ends of the long bones, has a variable amount of cortical shells with a deeper trabecular structure, wherein the amount of cortical shells may vary greatly. Dense bone typically has small and closely spaced trabeculae, resulting in a hard and strong bone. In comparison, less dense or osteoporotic bone has larger and more widely spaced trabeculae, typically resulting in a softer and generally weaker bone. This less dense bone generally comprises a cancellous bone region about the intermedulary canal. A typical bone structure thus typically includes a cortical layer atop cancellous layer where the proportion of both types of bone may vary. Since the structure of bone may vary significantly from one area of the body to another, the specific performance characteristics required of a suture anchor also vary accordingly. Therefore, suture anchors must be able to function as intended when used in all types of bone structure. Where suture anchors are implanted into dense bone structures, well-defined strong gripping edges are required for the suture anchor to securely engage the bore in the bone. However, where the suture anchor is implanted into less dense bone, a large surface area engaging the bone is preferred in order to distribute and reduce the stresses on the relatively weak bone.

Several factors determine whether the implantation of a particular suture anchor will be effective. For example, wedge-type suture anchors generally depend on the rotation of the suture anchor within the bore in order to allow the gripping edges to interact with the wall of the bore to secure the suture anchor in place. Accordingly, the suture anchor must often be inserted into the bore in a particular orientation, which must be maintained in order to prevent the gripping edges of the suture anchor from engaging the wall of the bore until the suture anchor has been inserted to the proper depth. However, the suture anchor, once inserted to the desired depth in the bore, must then be properly seated by rotating the suture anchor such that the gripping edges engage the wall of the bore to optimally secure the suture anchor in the bone. Both of these factors should be considered in order to provide an effective suture anchor system.

The Luscombe et al. '418 patent and the Pedlick et al. '538 patent each disclose wedge-type suture anchors which are angularly shaped, generally approximating a triangle to a quadrilateral and having straight sides. According to one aspect of these references, an insertion tool is used for implanting the suture anchor in the bore, wherein the insertion tool is configured to have a frangible portion at or near the interface of the insertion tool and the suture anchor. The frangible portion is further configured to break or separate from the suture anchor after implantation thereof in the bore. However, the frangible portion of the insertion tool may limit the orientation at which the suture anchor may be introduced to and inserted into the bore without fracturing the frangible portion. Such limited mobility may also cause the gripping edges of the suture anchor to engage the wall of the bore before the proper implantation depth has been attained. Accordingly, the limited mobility of the insertion tool having a frangible portion may not facilitate rotation of the suture anchor and may render it difficult to attain a seated position for the suture anchor before breakage of the frangible portion. Where a seated position has not been attained, a tensile force on the suture engaged with the suture anchor may undesirably be required in addition to or in the alternative to a tensile force on the insertion tool.

The application of a tensile force on the suture to seat the suture anchor may not be desirable for several reasons. For example, since the seating force for the suture anchor is applied by an individual, it would be very difficult to achieve the desired seating force, much less a consistent seating force, between applications. In addition, the location of the bore in the suture anchor through which the suture is looped may not be appropriately located on the suture anchor to allow a tensile force on the suture to provide any rotational force for seating the suture anchor. As such, the suture anchor may not be properly seated if the seating force is insufficient and the suture anchor may thus not provide the necessary securing force for securing the adjacent tissue to the bone. Alternatively, the suture may be broken or pulled out of the suture bore, or the suture anchor broken or pulled out of the bore, if the seating force is exceeded. Accordingly, in these instances, the implantation procedure may have to be performed again and at a different site, using a new suture anchor. Still further, it may also be difficult to design and manufacture a suture anchor having the necessary mechanical properties for implantation according to this procedure.

In the alternative, Luscombe et al. '418 patent, the Pedlick et al. '538 patent, and the Bartlett '718, '612, '863, '503, '372, '408, and '158 patents each describe a discrete flexible metallic insertion tool comprised of, for example, a shape memory material, which engages a bore in the anchor in a friction fit. Such flexible insertion tools may be beneficial in maintaining the suture anchor in a desired orientation upon insertion thereof into the bore, as well as for facilitating the manipulation or rotation of the suture anchor toward a seated position. However, since the insertion tool is only engaged with the suture anchor via a friction fit and thus may be easily separated therefrom, a tensile force directly on the suture engaged with the suture anchor may be required in order for the suture anchor to attain a seated position. Alternatively, the suture may be held against or secured to the insertion tool to maintain the insertion tool in engagement with the suture anchor such that the necessary tensile force can then be applied on the insertion tool to seat the suture anchor. Accordingly, in either instance, the tensile seating force is undesirably applied to the suture anchor via the suture.

Still further, the Pedlick et al. '538 patent describes a threaded connection between the suture anchor and a flexible insertion tool. However, such threaded components may be difficult and time-consuming to form on both the suture anchor and the insertion tool. Further, the suture anchor may undesirably rotate about the axis of the insertion tool during the suture anchor seating process, thus making it difficult to rotate the suture anchor toward the seated position within the bore. In addition, it may also be very difficult to appropriately configure the threads to attain and consistently control the seating force which may be applied on the suture anchor and/or the necessary force for separating the insertion tool from the suture anchor. In some instances, a seating force applied on the insertion tool may strip the threads in the suture anchor or cause other damage thereto. If, in these instances, the suture anchor is not properly seated, the stripped threads would prohibit the insertion tool from being re-engaged with the suture anchor so as to further apply a seating force and thus the undesirable application of the seating force directly to the suture may be the only remaining option.

Thus, there exists a need for a suture anchor system having the desirable suture anchor implantation characteristics of a flexible insertion tool comprised of a shape memory material, while allowing a predetermined seating force to be applied on the suture anchor before the insertion tool is removed from the suture anchor following insertion thereof in the bore. Such a system would desirably provide predetermined and consistent seating characteristics of the suture anchor in the bone.

BRIEF SUMMARY OF THE INVENTION

The above and other needs are met by the present invention which, in one embodiment, provides a suture anchor system configured so as to facilitate implantation of a suture anchor within a bore formed in a bone so as to secure a suture to the bone. Such a system comprises a suture anchor having a suture operably engaged therewith and an insertion tool having a tip and defining a first axis. The insertion tool is discrete with respect to the suture anchor and is capable of implanting the suture anchor within the bore such that the suture anchor is secured in the bone. The tip is engagable with the suture anchor and is configured to cooperate therewith so as to prevent the suture anchor from rotating about the first axis. Further, the insertion tool is configured with respect to the suture anchor such that a rotational force exerted on the insertion tool rotates the suture anchor about a second axis disposed perpendicularly with respect to the first axis. A predetermined axial seating force is then applied to the insertion tool, outwardly of the bore, to seat the suture anchor in the bore. The insertion tool is further configured so as to require an axial separation force to be applied thereto so as to separate the insertion tool from the suture anchor, wherein the separation force is no less than the seating force.

Another advantageous aspect of the present invention comprises a method of implanting a suture anchor in a bore in a bone, wherein the suture anchor has a suture operably engaged therewith, so as to secure the suture to the bone. The suture anchor is first inserted into the bore with a discrete insertion tool having a tip and defining a first axis. The tip is engaged with the suture anchor and cooperates therewith to prevent the suture anchor from rotating about the first axis. A rotational force is then exerted on the insertion tool so as to rotate the suture anchor about a second axis perpendicularly disposed with respect to the first axis. An axial seating force is also exerted on the insertion tool, outwardly of the bore, so as to seat the suture anchor in the bore. The insertion tool is then separated from the suture anchor by exerting an axial separation force on the insertion tool, wherein the separation force is no less than the seating force.

Thus, embodiments of the present invention provide a suture anchor system having the desirable suture anchor implantation characteristics of a flexible insertion tool comprised of a shape memory material, while allowing a predetermined seating force to be applied on the suture anchor, by the insertion tool engaged therewith, before the insertion tool is removed from the suture anchor following insertion thereof in the bore, thereby providing predetermined and consistent seating characteristics of the suture anchor in the bone. Accordingly, embodiments of the present invention provide significant advantages as detailed herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
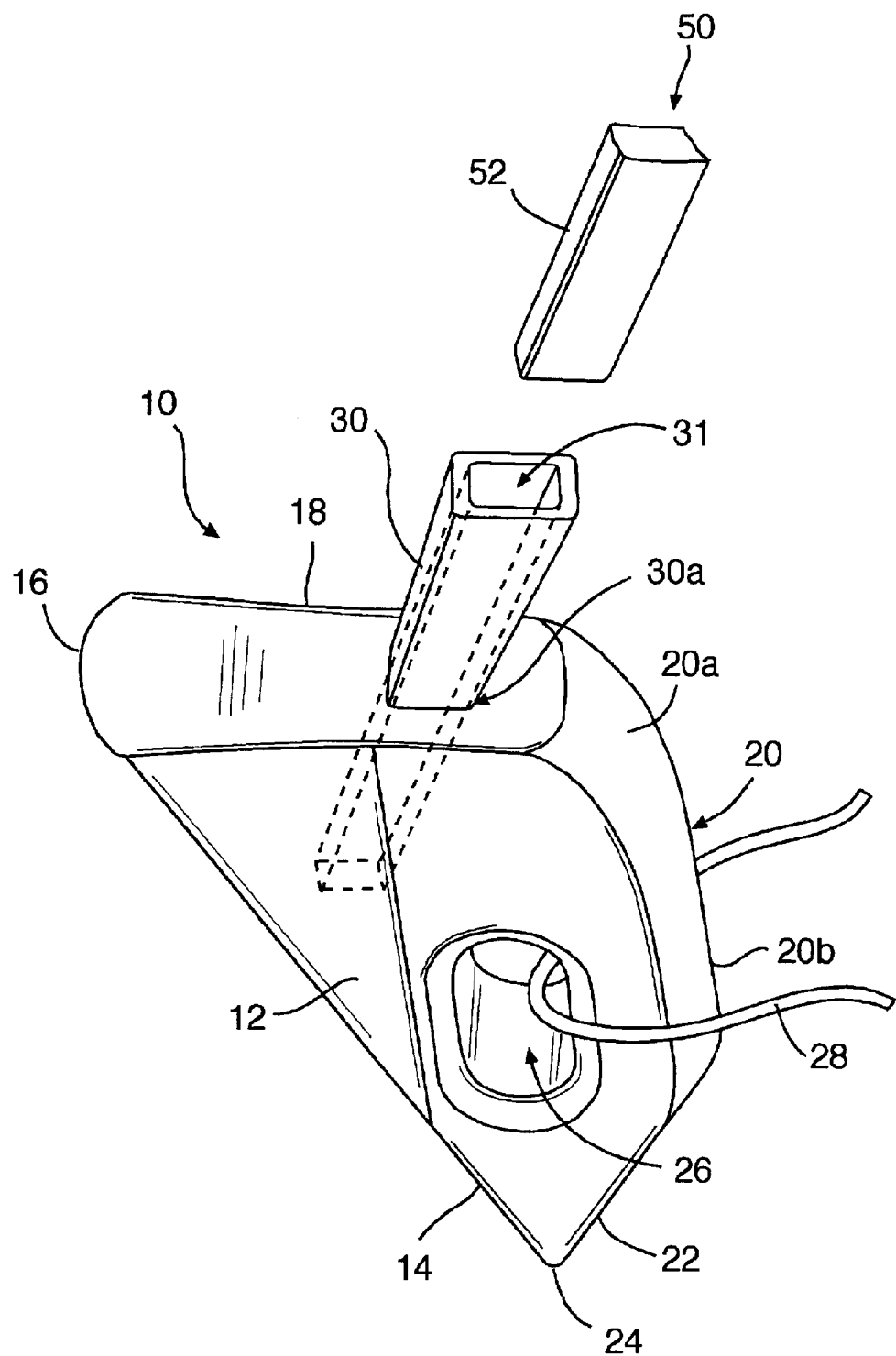
FIG. 1 is a perspective view of a suture anchor system according to one embodiment of the present invention illustrating a separator extension having a frangible portion.

FIG. 1 discloses one embodiment of a suture anchor system according to the present invention, the system being configured to allow a predetermined seating force to be applied on the suture anchor 10, by an insertion tool 50 engaged therewith, before the insertion tool 50 is removed from the suture anchor 10 following insertion thereof in the bore. A suture anchor 10 is described in, for example, U.S. Pat. No. 6,306,158 to Bartlett, and generally comprises a quadrilaterally shaped body 12 having a maximum length surface 14, a leading edge 16, a separator surface 18, an upper width surface 20, a lower width surface 22, a trailing edge 24, and a suture bore 26. The maximum length surface 14 and the separator surface 18 intersect at an acute angle to form the leading edge 16. At the other end, the maximum length surface 14 intersects with the lower width surface 22 at an acute angle to form the trailing edge 24. The separator surface 18 and the lower width surface 22 are further connected by the upper width surface 20, dispose generally opposite the maximum length surface 14 and comprising an arcuate portion 20a and a substantially linear portion 20b. The body 12 further defines a transverse suture bore 26 therethrough and through which a suture 28 extends. The leading edge 16 may be wide in order to distribute the anchoring stress over a greater surface area, as well as provide a more robust suture anchor 10. Though the present invention is described herein in terms of a suture anchor as disclosed in the Bartlett '158 patent, one skilled in the art will appreciate that the present invention may be implemented with many other configurations of suture anchors, such as those disclosed in the other references incorporated herein, and as such, the provided description is for exemplary purposes only and is not intended to be limiting with respect to the configuration of the suture anchor.

According to one particularly advantageous aspect of the present invention, the separator surface 18 is generally a flat surface and has a separator extension 30 extending therefrom. The separator extension 30 extends from the separator surface 18 at a predetermined inserter angle, with respect to the maximum length surface 14, wherein the inserter angle is configured such that the insertion tool 50 is capable of simultaneously urging the maximum length surface 14 into the bore and against the wall of the bore when the suture anchor 10 is first inserted therein. In addition, the separator extension 30 includes a frangible portion 30a in proximity with the separator surface 18, wherein the frangible portion 30a is configured to have a predetermined tensile breaking strength. That is, the frangible portion 30a is configured with respect to, for example, shape, dimensions, and other factors, such that a tensile force of at least a predetermined magnitude may be applied on the separator extension 30 before breakage of the frangible portion 30a and separation of the separator extension 30 from the suture anchor 10 occurs. Accordingly, the separator extension 30 is configured so as to engage at least a portion of the tip 52 of the insertion tool 50 such that the separator extension 30 is secured to the tip 52, and the tip 52 extends into the body 12 of the suture anchor 10, for reasons which are further discussed below.

Figure 1A:
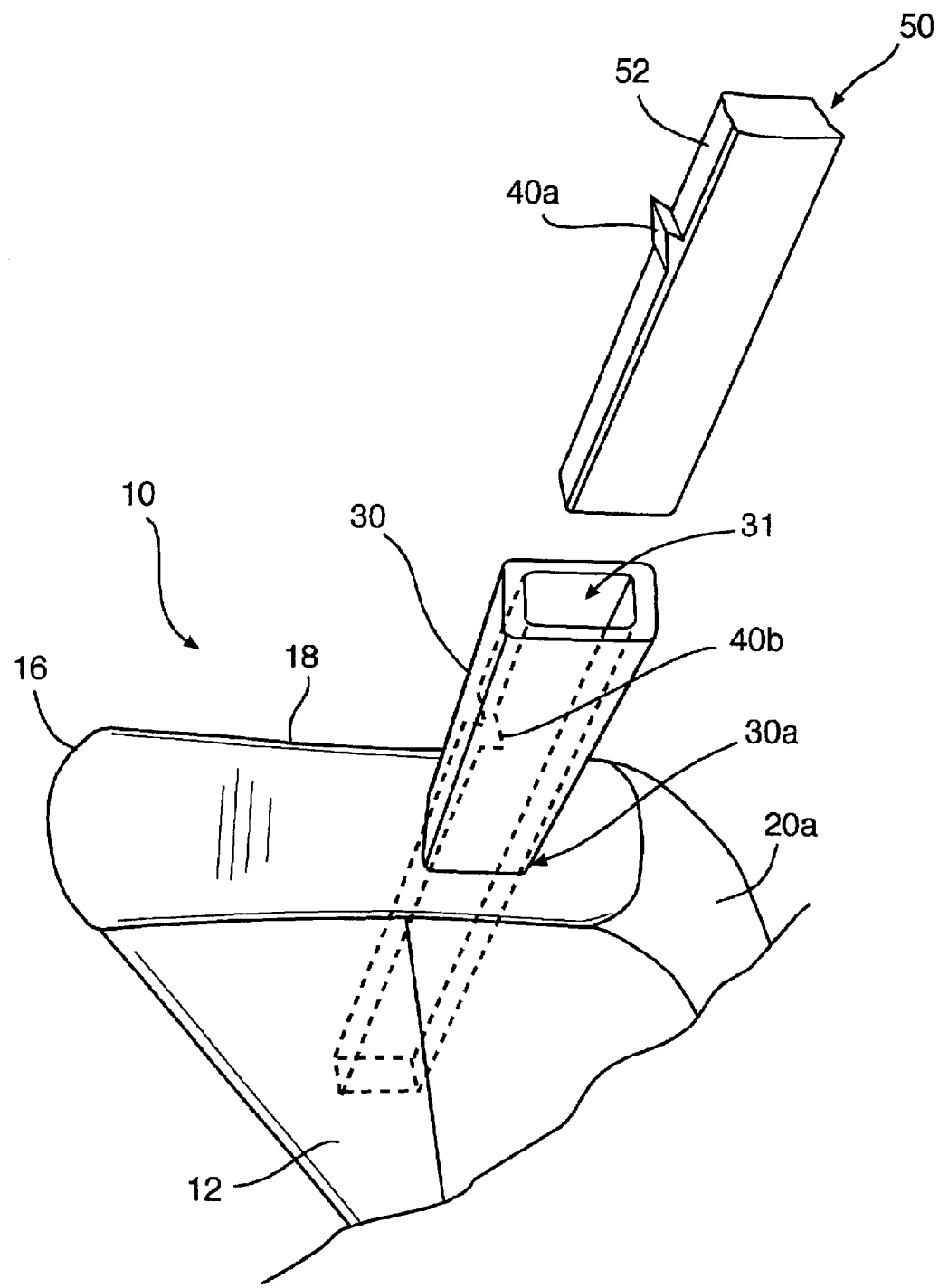
FIG. 1A is a perspective view of a suture anchor system according to one embodiment of the present invention illustrating an example of a retaining mechanism between the insertion tool and the separator extension.

In addition, the tip 52/separator extension 30 interface is configured so as to be capable of withstanding a tensile force greater than the predetermined breaking strength of the frangible portion 30a. In some instances, the tip 52 and the separator extension 30 may be configured to be separably engaged while having the necessary properties as discussed herein. Preferably, however, the frangible portion 30a is configured to have a breaking strength no less than the predetermined required seating force of the suture anchor 10. Further, the tip 52, the separator extension 30, and/or the body 12 are preferably configured to cooperate such that the separator extension 30 and body 12 are prevented from rotating about the axis of the tip 52. For example, the tip 52 may have a generally square cross-section configured to engage a correspondingly square bore 31 defined by the separator extension 30 and the body 12. In addition, the tip 52 may be retained in the bore 31 through, for instance, a mechanical connection, adhesive, or other suitable mechanism, which may, in some instances, be combined with a friction fit configuration. One example of a mechanism for retaining the tip 52 within the bore 31 is shown in FIG. 1A, wherein a first portion of the mechanism 40a engaged with the tip 52 cooperates with a second portion of the mechanism 40b engaged with the bore 31 when the tip 52 is inserted into the bore 31 to thereby retain the tip 52 in response to a tensile force exerted on the tip 52 outwardly of the bore 31. Also note that the separator extension 30 may not necessarily extend entirely about the tip 52 as shown in FIG. 1, but may only engage, for example, one, two, or three of the sides of a square tip 52, wherein the tip 52/separator extension 30 interface is appropriately configured to accomplish the securing of the tip 52 to the separator extension as discussed herein. Regardless of the configuration of the separator extension 30 and the interface thereof with the tip 52, which may take many different forms as will be appreciated by one skilled in the art, the body 12 will define the bore 31 for receiving the tip 52 if not readily apparent in the configuration of the separator extension 30.

Figure 1B:
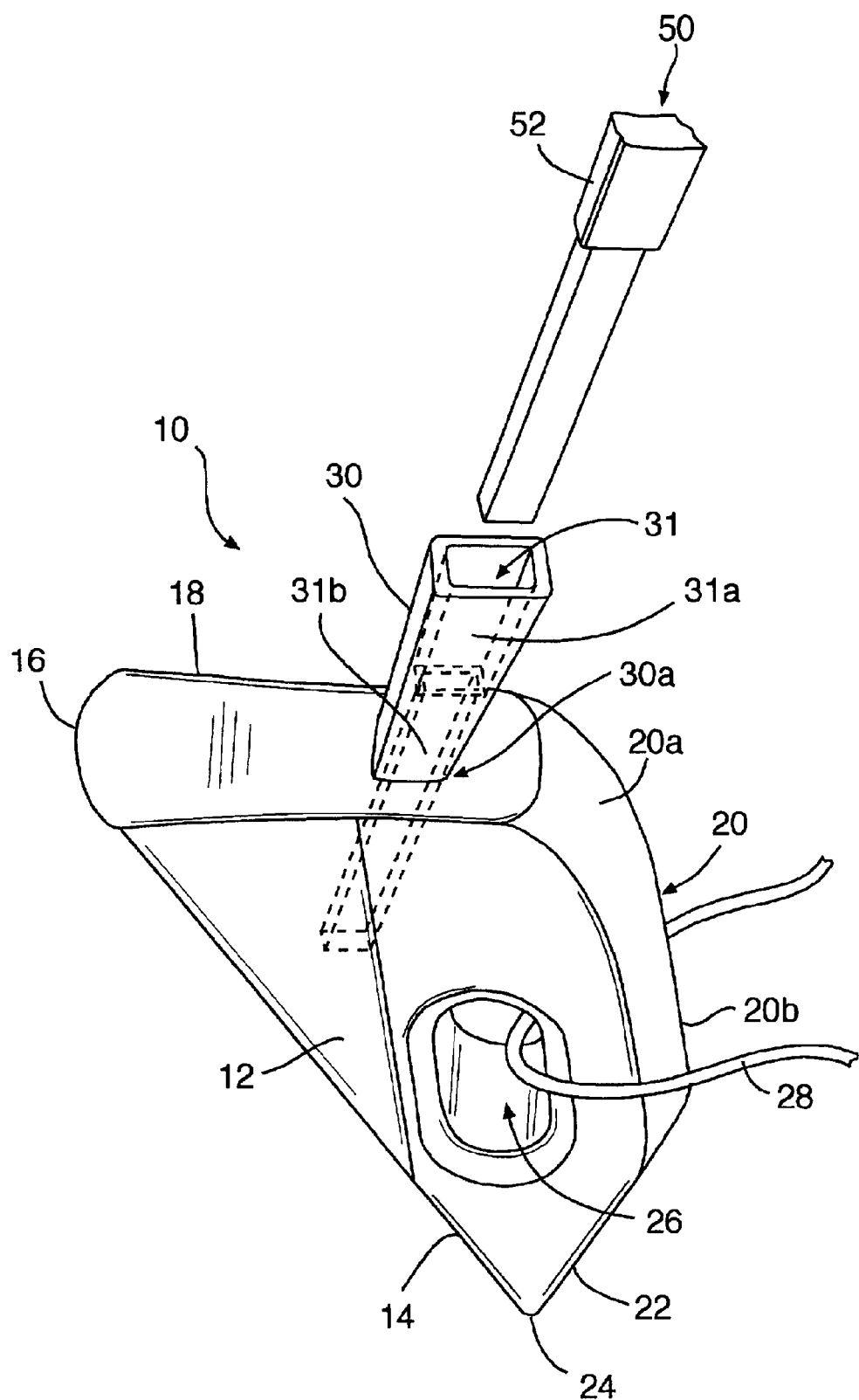
FIG. 1B is a perspective view of an alternate embodiment of a suture anchor system according to the present invention illustrating a separator extension having a tiered bore.

Since the frangible portion 30a must be sufficiently configured to withstand a rotational force on the insertion tool 50 for rotating the suture anchor 10 toward a seated position, the interaction of the insertion tool 50 with the separator extension 30 and the suture anchor 10 may take many different configurations. For example, as shown in FIG. 1B, the separator extension 30 may define a tiered bore 31 for receiving a correspondingly shaped tip 52. The larger tier 31a of the bore 31 may extend only into the separator extension 30, while the smaller tier 31b of the bore 31 may extend through the separator extension 30 and the frangible portion 30a and into the body 12 of the suture anchor 10. In such a configuration, the larger portion of the tip 52 may be secured to the larger tier 31a through, for instance, a mechanical connection, adhesive, or other suitable mechanism, while the smaller portion of the tip 52 is not secured in the smaller tier 31b. Accordingly, the smaller portion of the tip 52 essentially reinforces the frangible portion 30a for withstanding the stresses experienced during the rotation of the suture anchor 10 toward a seated position by the insertion tool 50. However, when the axial seating force is applied to the insertion tool 50 to seat the suture anchor 10, the tip 52 is only secured to the separator extension about the larger tier 31a and thus the frangible portion 30a will break at the predetermined breaking strength and allow the insertion tool 50 to be separated from the suture anchor 10. One skilled in the art will also appreciate that the structure of the tip 52 and the corresponding receiving bore 31 may take many different forms capable of accomplishing the described purpose. For example, the tip 52 may be tapered to engage a corresponding taper of the bore 31 extending into the body 12.

A suture anchor 10 according to the present invention is preferably biocompatible and, in some instances, is comprised of a bioabsorbable material, such as polylactic acid, polydioxanone, polyglycolic acid, and similar materials or blends thereof. Such materials should preferably be recognized by the appropriate regulatory authority as being suitable for use in humans. Additionally, it is desirable that the material strengthen the bone into which the anchor is inserted. It is further desirable for the material to be translucent or transparent to noninvasive examinations such as radiographs (e.g., X-rays). Accordingly, the suture anchor may also be comprised of cortical bone, where the bone may further be autologous or autogenous bone. More generally, the suture anchor may be comprised of a suitable biocompatible polymer, biocompatible metal, or other biocompatible material (see, e.g., U.S. Pat. Nos. 5,540,718, 5,626,612, 5,782,863, 5,871,503, 5,879,372, 6,146,408, and 6,306,158 to Bartlett, U.S. Pat. No. 5,683,418 to Luscombe et al., and U.S. Pat. No. 5,961,538 to Pedlick et al.). Further, such suture anchors 10 as described herein may be formed by many different processes such as, for example, casting, machining, molding, or the like, as will be appreciated by one skilled in the art.

Figure 2:
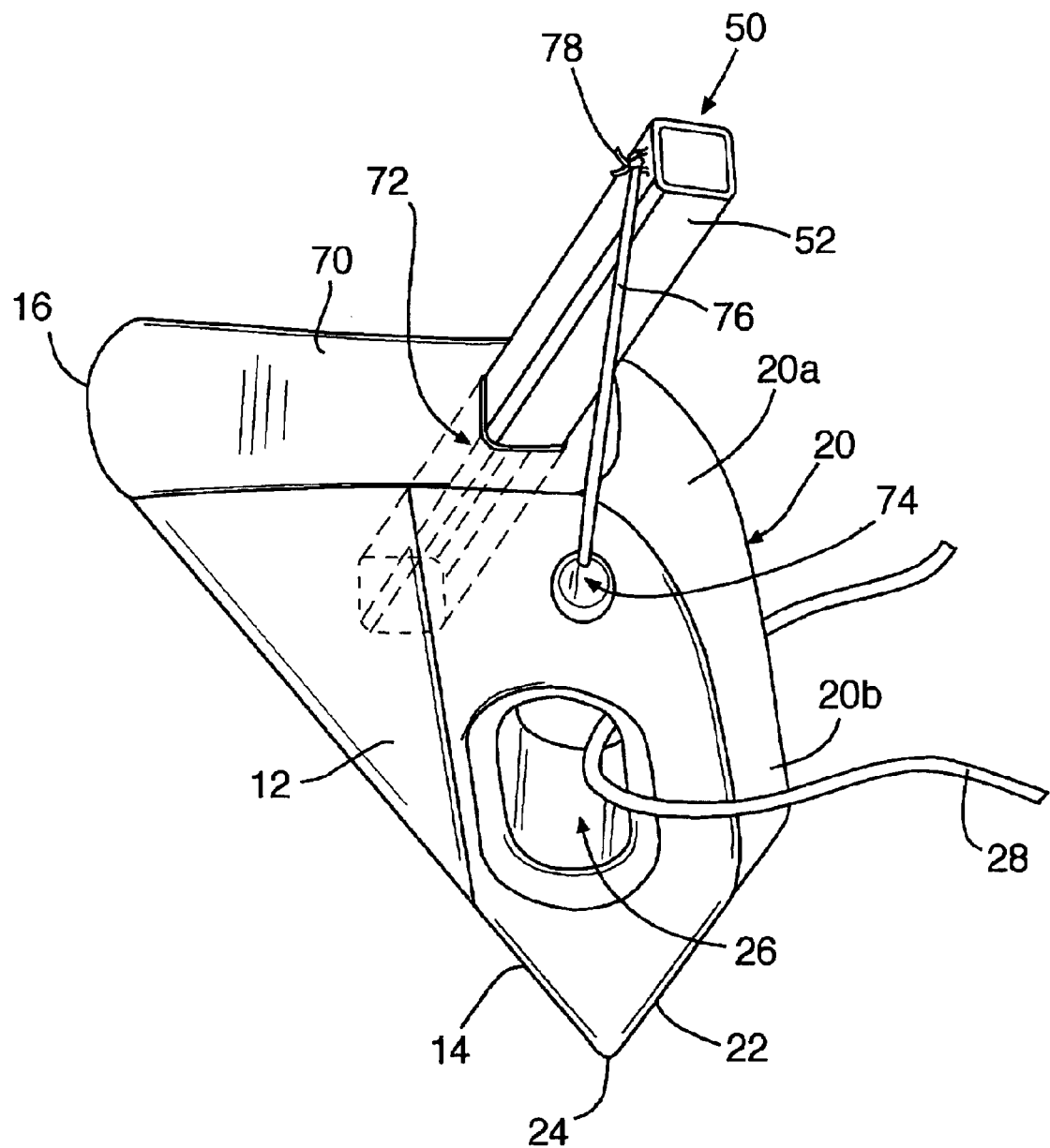
FIG. 2 is a perspective view of another alternate embodiment of a suture anchor system according to the present invention illustrating a tether securing the insertion tool to the suture anchor.

In an alternate embodiment of the present invention, as shown in FIG. 2, the suture anchor 10 is similar to that shown in FIG. 1, with the exceptions that the body 12 includes an inserter bore surface 70 defining an inserter bore 72 extending into the body 12. The inserter bore 72 is preferably located in the inserter bore surface 70 in the vicinity where the inserter bore surface 70 meets the arcuate portion 20a of the upper width surface 20. The inserter bore 72 extends into the body 12 towards the maximum length surface 14, wherein the obtuse angle between the inserter bore surface 70 and the maximum length surface 14 defines an inserter angle. The inserter bore 72 is configured to receive the tip 52 of the insertion tool 50 for implanting the suture anchor 10 within the bone. Preferably, the inserter bore 72 and the tip 52 have corresponding non-circular lateral cross-sections, such as generally square cross-sections having beveled or radiused corners, so as to prevent rotation of the suture anchor 10 about the axis of the tip 52. Generally, however, the tip 52 of the insertion tool 50 and the inserter bore 72 may have any corresponding shapes or configurations which minimize rotation of the suture anchor 10 about the axis of the tip 52. In addition, the suture anchor 10 may further define a tether bore 74 having a tether 76 extending therethrough. The tether 76 and the insertion tool 50 are configured such that the tether 76 is capable of engaging the insertion tool 50 so as to secure the tip 52 of the insertion tool 50 in engagement with the inserter bore 72 via the tether bore 74. In some instances, however, the tether 76 may secure the insertion tool to the suture anchor 10 via the suture bore 26. In either instance, the tether 76 may form a loop through the tether bore 74/suture bore 26 and about the insertion tool 50, wherein the loop may be terminated with an appropriate knot 78 or other connector. Such a tether 76 may comprise, for example, a suture or other suitable material capable of securing the suture anchor 10 to the insertion tool 50 and providing the necessary separation force. Accordingly, the tether 76 and/or the knot 78 may be configured so as to break at a predetermined separation force exerted on the insertion tool 50, wherein the separation force is no less than the required seating force for seating the suture anchor 10 in the bore, as detailed further herein.

As with the embodiment discussed in FIG. 1, and as contemplated for the embodiment shown in FIG. 2, at least the tip 52 of the insertion tool 50 is comprised of a material having elastic properties and, more preferably, superelastic properties, such as, for example, a shape memory material. The elastic or superelastic properties of the material should be such that the tip 52 is not substantially permanently deformed during insertion and implantation of the suture anchor 10, thereby allowing the tip 52 to substantially return to an initial configuration, namely the configuration of the tip 52 as it is initially inserted into the inserter bore 72. Preferably, at least the tip 52 of the insertion tool 50 is comprised of a nickel-titanium alloy, such as is commercially available under the names NITINOL™ by Raychem, TINEL™ by Raychem, or SENTINOL™ by GAC International Inc. Such shape memory alloys having superelastic properties are well known in the art; however, any other shape retaining material sufficient for properly implanting the suture anchor 10 of the present invention in a bore in a bone may be used. The use of a shape memory material and the shape of the tip 52 which minimizes rotation of the suture anchor 10 about the tip 52 engaged therewith further allows a smaller sized tip 52 to be used to effectively implant the suture anchor 10 within a bone. In addition, a smaller sized tip 52 further allows a smaller suture anchor 10 to be used in situations where such is necessary or desired.

The suture anchor 10 may include a suture 28 engaged therewith through the suture bore 26. The suture bore 26 may vary in size and is preferably rounded or beveled around the openings in the body 12 in order to avoid abrasion of the suture 28. In addition, the inserter bore 72 is generally disposed intermediate the leading edge 16 and the suture bore 26. As described further herein, the inserter bore 72 cooperates with the insertion tool 50 to introduce the suture anchor 10 into a bore in a bone. As the suture anchor 10 is introduced into the bore, the maximum length surface 14 lies flush with the wall of the bore, with the insertion tool 50 imparting a force component sufficient to urge the maximum length surface 14 against the wall. The upper width surface 20 and, more specifically, the arcuate portion 20a, is thus disposed adjacent to the wall of the bore diametrically opposite the maximum length surface 14. Once the suture anchor 10 is inserted to a sufficient depth within the bore, the flexed tip 52 will tend to return to its initial configuration and thereby initiate rotation of the suture anchor toward a seated position. Thereafter, the rotation of the suture anchor 10 may be furthered by moving the insertion tool 50 to the diametrically opposite side of the bore from which the insertion tool 50 initially introduced the anchor 10 into the bore. According to one advantageous aspect of the present invention, an axial separation force is then exerted on the insertion tool 50, outwardly of the bore, such that the separation force acts on the suture anchor to rotate the suture anchor 10 into a seated position in the bore. The suture anchor 10 generally requires a certain seating force to be exerted thereon to rotate the suture anchor 10 within the bore in the bone until a seated position is attained, wherein the seated position is up to about ninety degrees from the orientation in which the suture anchor 10 was initially inserted into the bore and the degree of rotation depends, at least in part, on the structure of the bone into which the suture anchor 10 is implanted. Thus, the tether 76 and/or the knot 78 are preferably configured to have a breaking strength, otherwise referred to herein as the separation force required to separate the insertion tool 50 from the suture anchor 10, of no less than the seating force for the suture anchor 10. In some instances, the separation force may be slightly greater than the seating force, but less than the pullout strength of the suture anchor 10 itself, such that the suture anchor 10 can be checked for proper seating by repeated applications of the seating force before the tether 76 is broken and the insertion tool 50 removed from the suture anchor 10. Such suture anchors 10 as described herein are often configured to be seated in the bore such that the pullout strength, or the force required to extract a seated suture anchor 10 from the bore, approaches the tensile strength of the suture 28 threaded therethrough. For example, the suture anchor 10 and attached suture 28 may be configured to withstand a force of up to about 30 pounds without the suture anchor 10 pulling out of the bore or the suture 28 breaking. This relationship between the separation force and the seating force may also be applicable and beneficial to the embodiment illustrated in FIG. 1 and other embodiments of the present invention.

Figure 3:
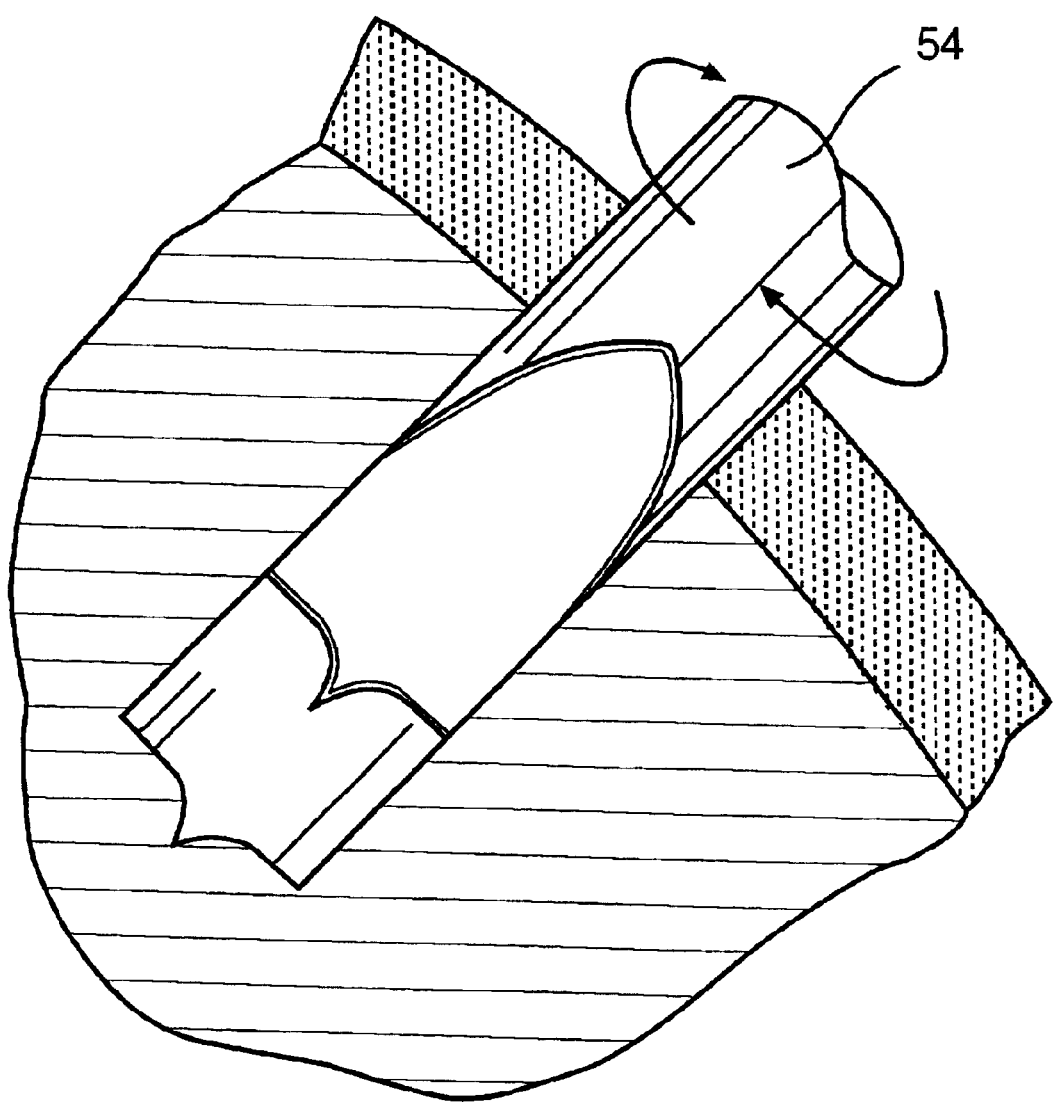
FIGS. 3–10 illustrate a cross-sectional sequence of the insertion of a suture anchor, as shown in FIG. 2, into a bore in a bone in accordance with one embodiment of the present invention.
Figure 4:
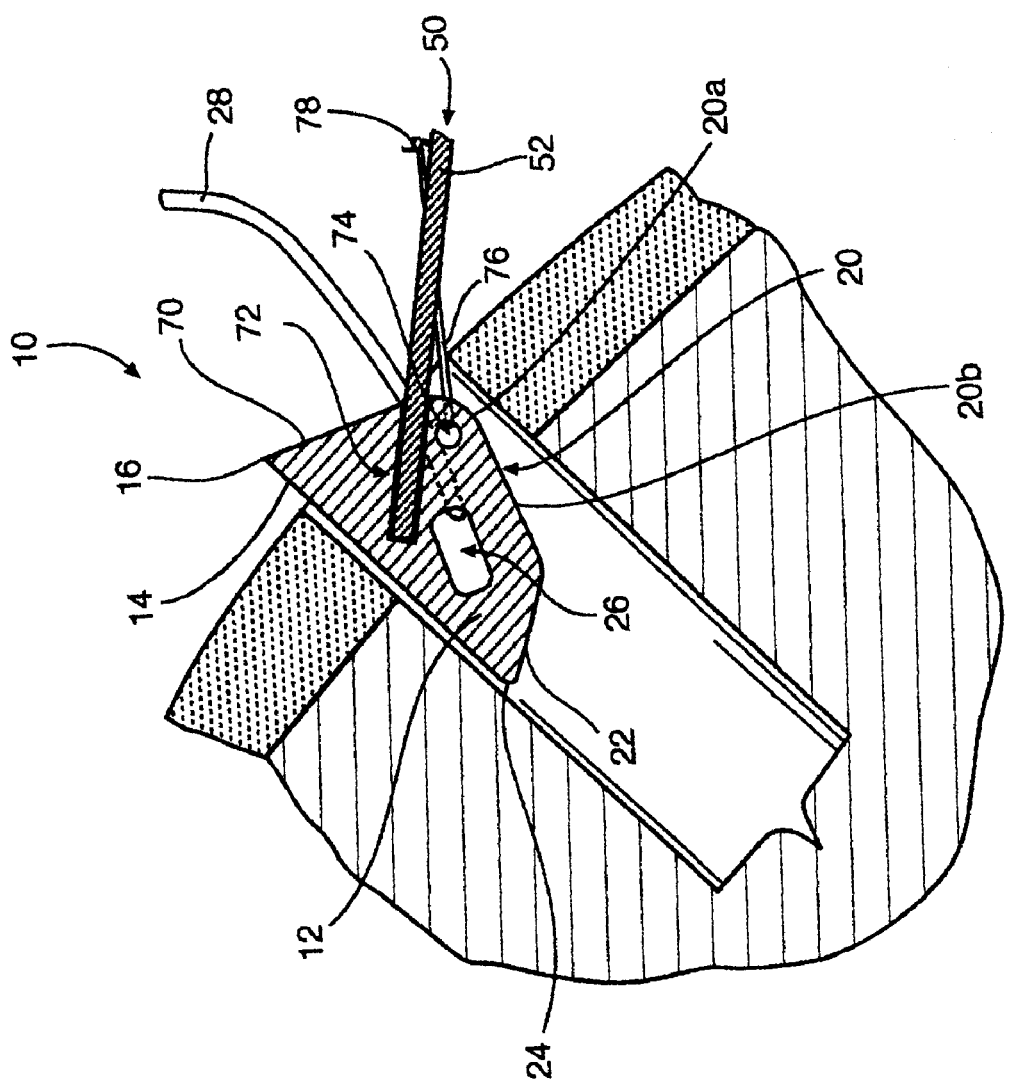

FIGS. 3–10 illustrate a method of implanting a suture anchor 10 within a bore in a bone according to one embodiment of the present invention using an embodiment of a suture anchor system as illustrated in FIG. 2. As shown in FIG. 3, a bore is first drilled in the bone using a boring bit 54. The bore generally passes through an outer layer of dense bone (cortical layer) and into an inner layer of a less dense or osteoporotic bone (cancellous layer) further therein. Once the bore is formed, the boring bit 54 is removed. As shown in FIG. 2, the inserter bore 72 of a suture anchor 10 is then engaged with the tip 52 of the insertion tool 50, the suture anchor 10 including a suture 28 threaded through the suture bore 26. The suture anchor 10 is secured to the tip 52 or other portion of the insertion tool 50 by a tether 76 extending through the tether bore 74 to the insertion tool 50. The loose ends of the suture 28 are also held against the insertion tool 50 in order to prevent the suture 28 from becoming tangled or damaged during the insertion process. As shown in FIG. 4, the suture anchor 10 is then introduced into the bore such that the maximum length surface 14 is engaged with the wall of the bore. In this position, the insertion tool 50 is in its original configuration (substantially straight), with the tip 52 inserted in the inserter bore 72 and angled with respect to the axis of the bore. Further, as shown, the diameter of the bore roughly corresponds to the maximum width of the suture anchor 10. Thus, when the suture anchor 10 is introduced into the bore in the bone, the maximum length surface 14 is preferably contacting the wall of the bore, while the point defining the maximum width of suture anchor 10 is at least within close proximity to the wall of the bore diametrically opposite the maximum length surface 14.

Figure 5:
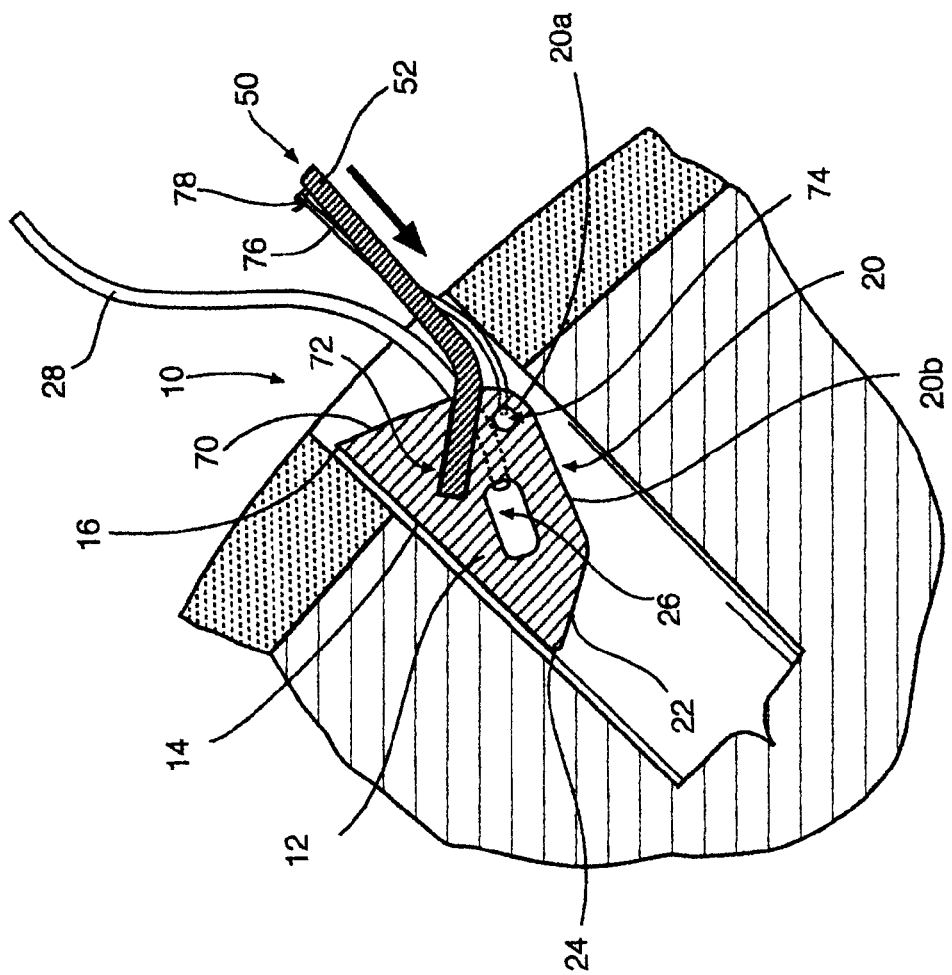

As shown in FIG. 5, a force directed inwardly with respect to the bore is then exerted on the insertion tool 50 such that the suture anchor 10 is urged into the bore. When the insertion tool 50 encounters the outer layer of cortical bone, the force causes the insertion tool 50 to bend such that distal end of the tip 52 remains in the inserter bore 72, but the portion of the tip 52 outside of the suture anchor 10 bends or deforms to conform to the wall of the bore. At this point, a portion of the maximum length surface 14 is still in contact with the dense cortical bone layer since suture anchor 10 has not been inserted far enough into the bore for the leading edge 16 to pass by the cortical bone layer. The maximum length surface 14, aided by the force provided by the tip 52 of the insertion tool 50, remains flush against the wall of the bore.

Figure 6:
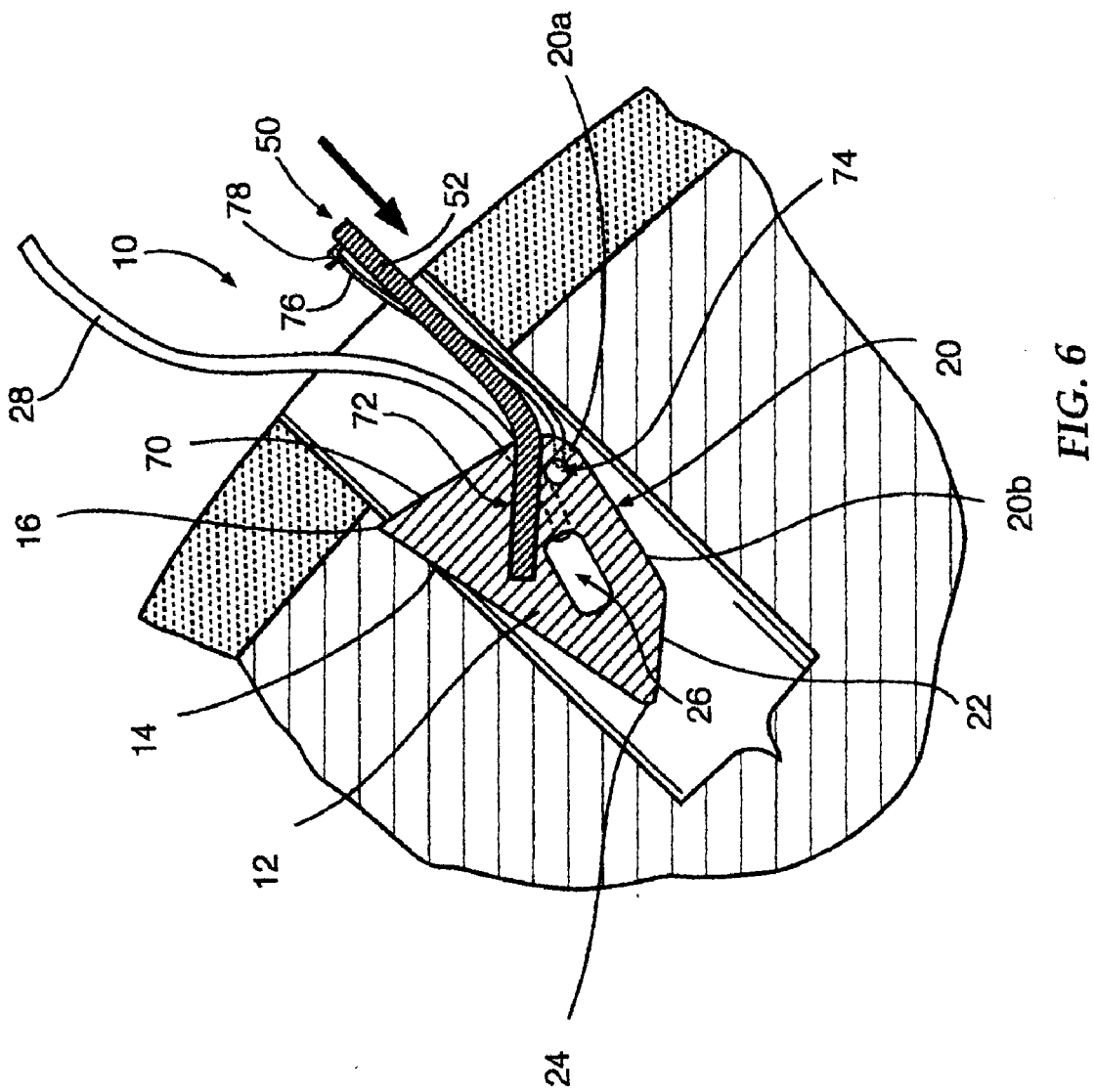
Figure 7:
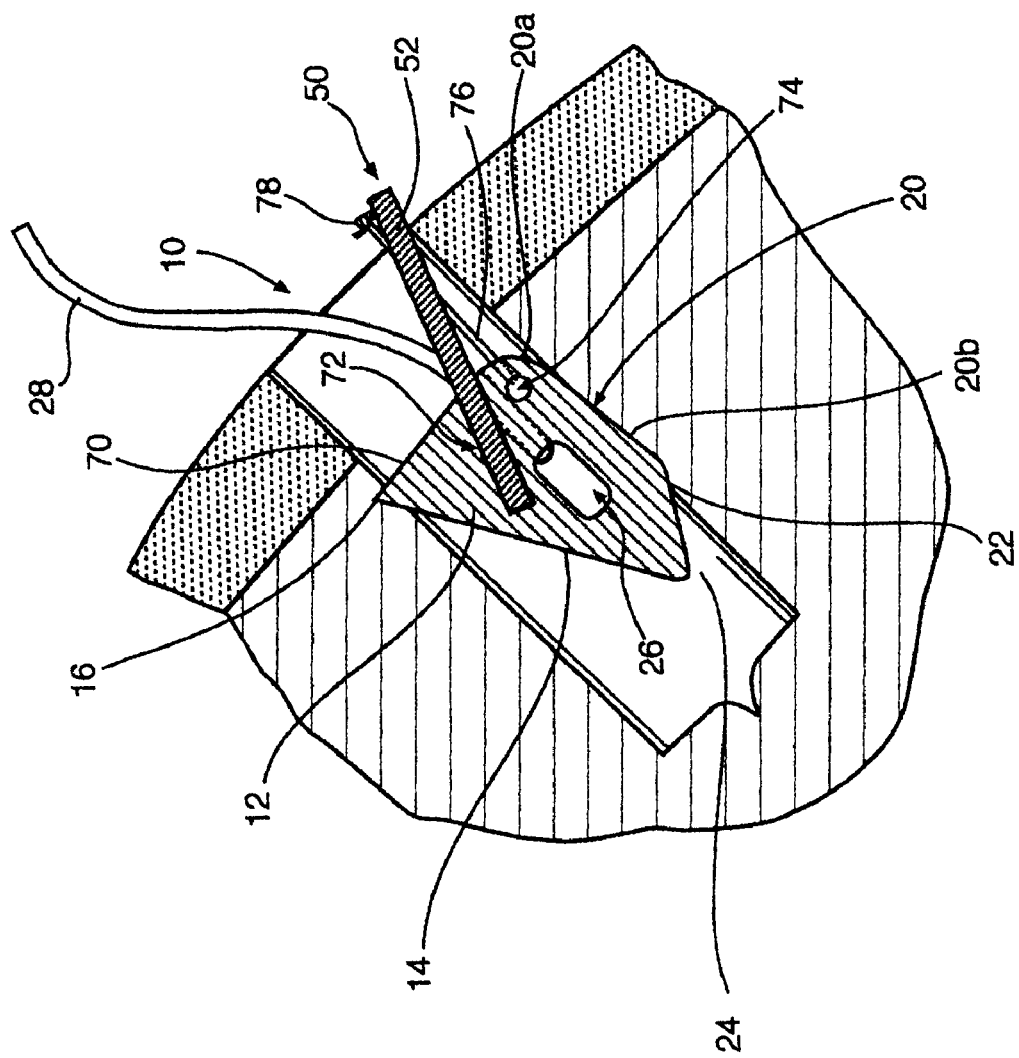

FIG. 6 shows the suture anchor 10 after further force has been exerted on the insertion tool 50 inwardly with respect to the bore. Once the suture anchor 10 has been inserted into the bore for a sufficient distance to clear the dense cortical surface layer of bone, it enters a less dense inner portion of the bone, namely the cancellous layer. Since the cancellous layer is less dense and weaker than cortical bone, the suture anchor 10 may begin to turn or rotate within the bore in response to force exerted by the tip 52 of the insertion tool 50 returning to its original shape due to the effect of the shape memory material from which it is comprised. As the rotation of the suture anchor 10 occurs, the leading edge 16 is forced into the cancellous layer forming this portion of the wall of the bore. Diametrically opposed the leading edge 16, the arcuate portion 20a is urged against the wall of the of the bore, wherein engagement with the wall proceeds along the arcuate portion 20a to the linear portion 20b and then to the lower width surface 22 as the suture anchor 10 rotates. Thus, the suture anchor 10 generally begins to rotate about the point where the leading edge 16 engages the wall of the bore. As further shown in FIG. 7, the rotation of the suture anchor 10 may continue until the tip 52 of the insertion tool 50 has returned to its original shape such that the insertion tool 50 rests against the wall at the entrance to the bore.

Note that the suture anchor 10 has been illustrated in this embodiment of a method of implantation as interacting with a bone structure having a cancellous layer underlying a cortical layer, such as that found, for example, in the "rotator cuff" area of the human shoulder (also known as the greater tuberosity of the humerus). However, a suture anchor 10 according to embodiments of the present invention may also be used in areas of dense bone, predominantly comprised of a cortical layer with an underlying cancellous layer having a relatively high density, such as, for example, at the "cup" or glenoid area of the shoulder. Note, however, that the density of the cancellous layer may vary greatly. While a suture anchor 10 according to embodiments of the present invention may tend not to rotate as freely or extensively within a cortical bone layer as within a cancellous layer, such a suture anchor 10 includes features further described herein which render the suture anchor 10 generally adapted for application to both dense cortical bone and less dense cancellous bone structures.

Figure 8:
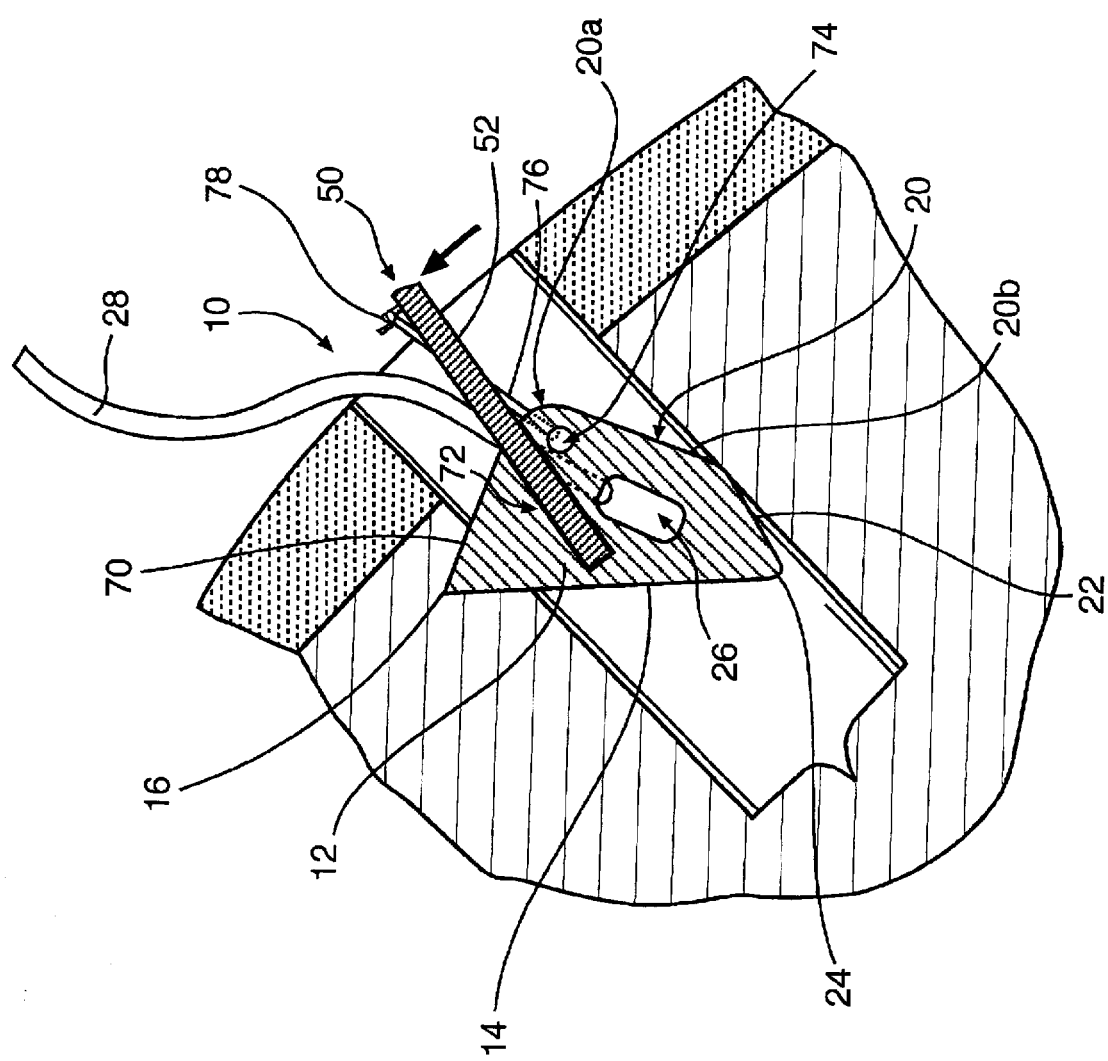
Figure 9:
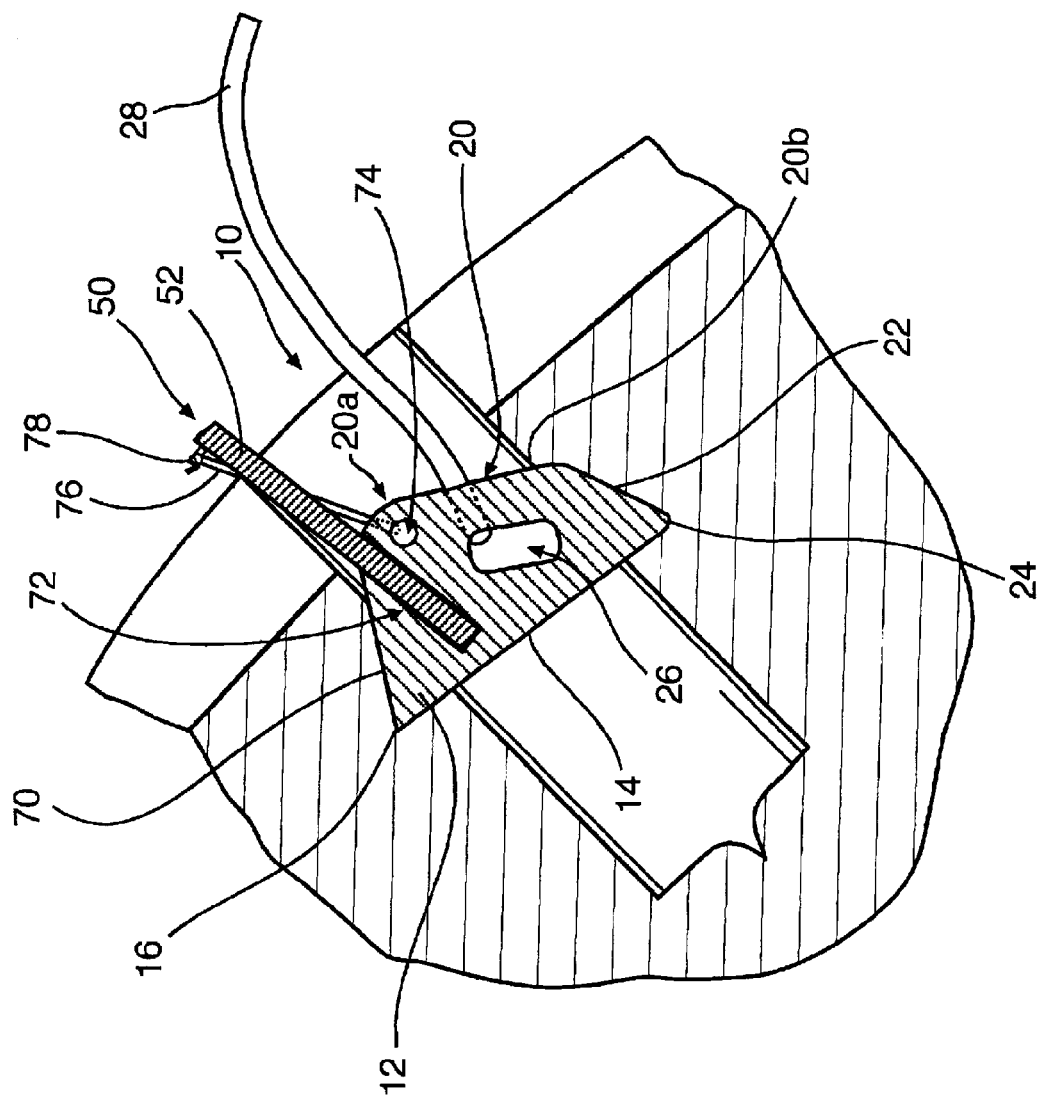

As shown in FIG. 8, further rotation of the suture anchor 10 may be obtained by exerting a rotational force on the insertion tool 50 so as to move the insertion tool 50 to the diametrically opposite side of the bore. The rotational force exerted on the insertion tool 50 causes the leading edge 16 to bite or penetrate further into the wall of the bore and the suture anchor 10 to rotate about the leading edge 16. That is, the rotation of the insertion tool 50 causes the suture anchor 10 to rotate about an axis perpendicular to the axis of the insertion tool 50. Accordingly, at the wall on the opposite side of the bore, the trailing edge 24 begins to penetrate into the wall of the bore. Note that, in some instances, the rotation of the insertion tool 50 may also be accompanied by an axial force exerted on the insertion tool 50 outwardly of the bore. In either event, at this point, the insertion tool 50 is in contact with the wall on generally the opposite side of the bore from which the insertion tool 50 initially entered the bore. However, the suture anchor 10 may not necessarily be in a seated position. Accordingly, an axial seating/separation force is then applied to the insertion tool 50, outwardly of the bore, so as to seat the suture anchor 10, as shown in FIG. 9.

Figure 10:
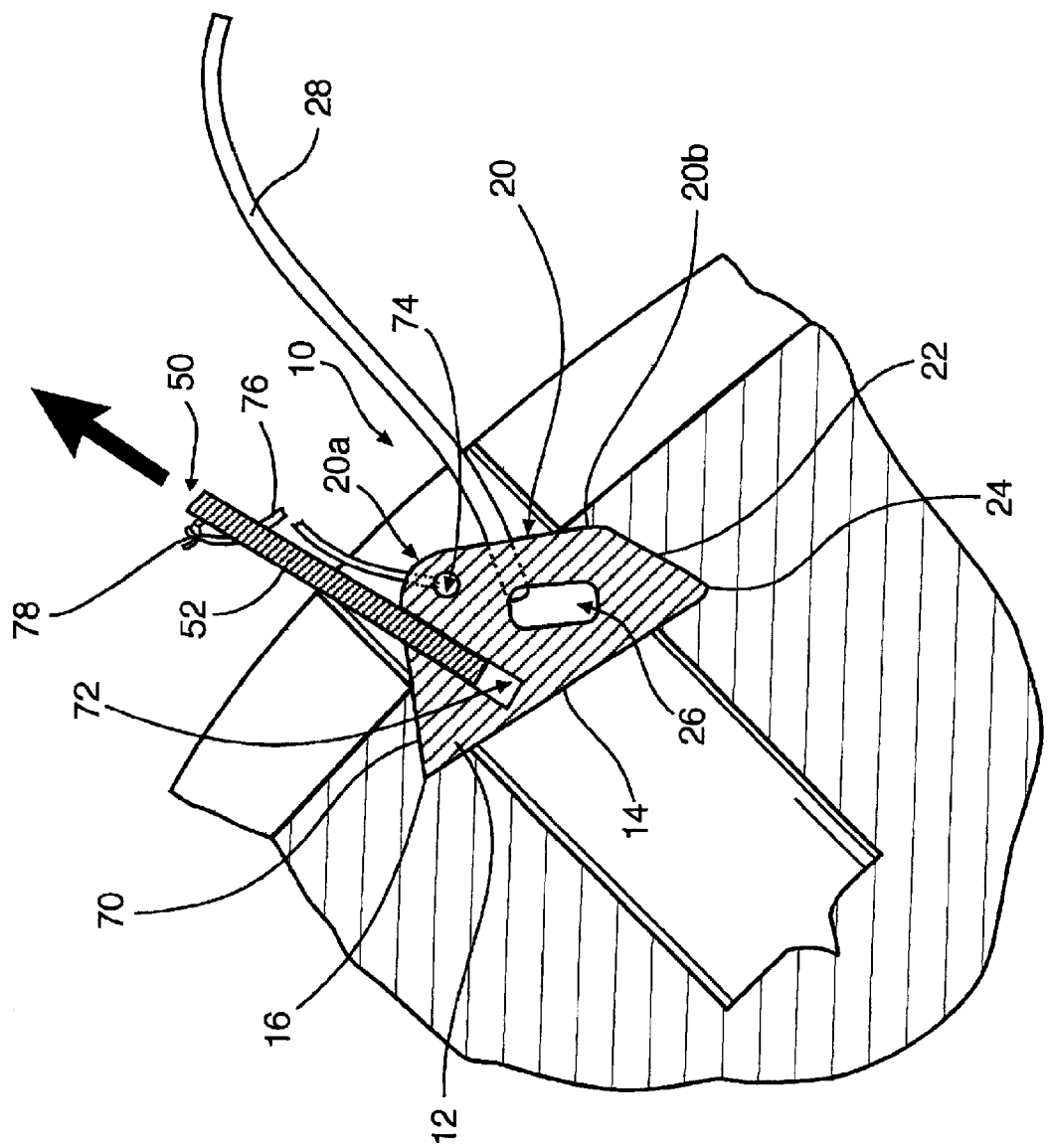
Figure 10A:
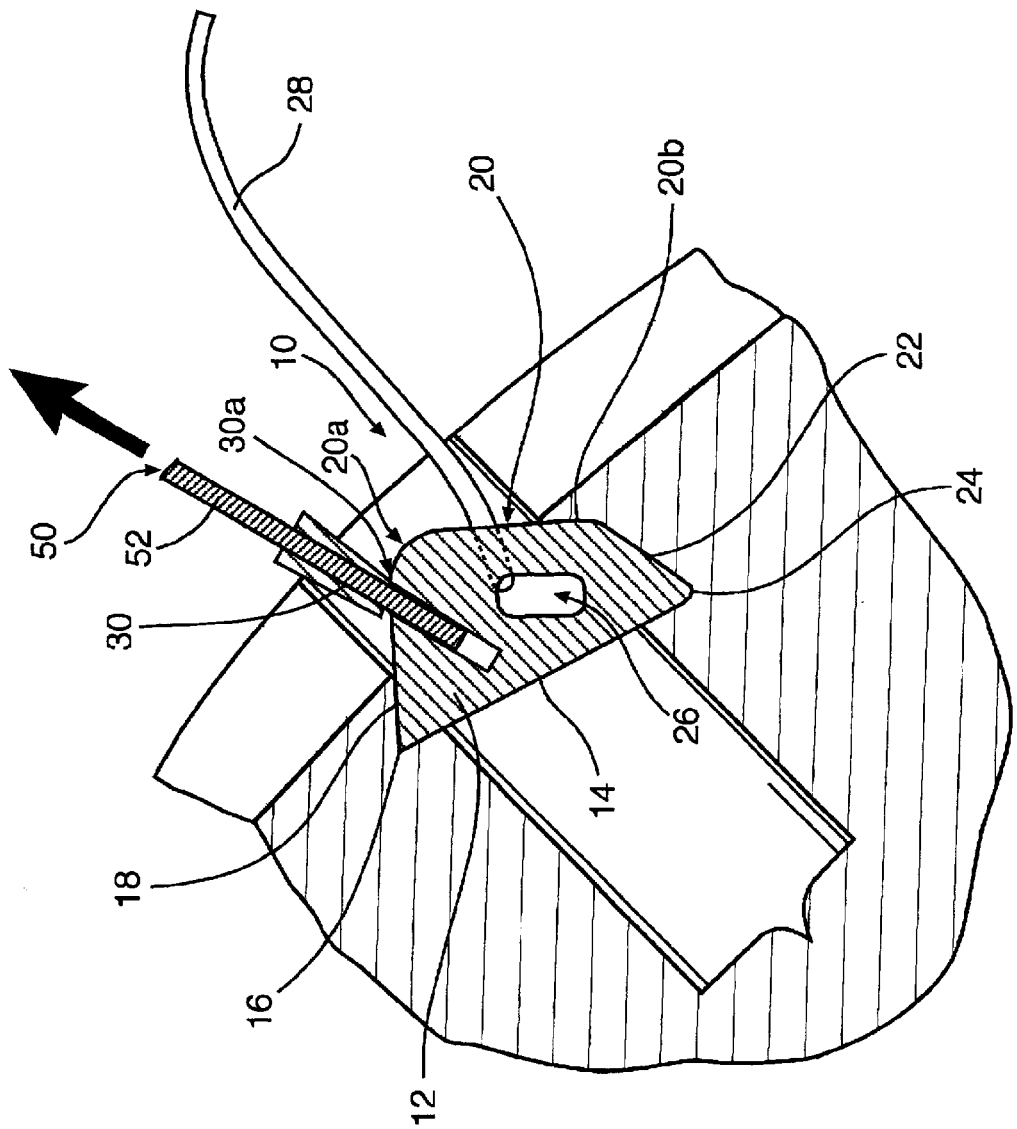
FIG. 10A is a cross-sectional view of a suture anchor, as shown in FIG. 1, being anchored within a bore in a bone in accordance with one embodiment of the present invention.
Figure 11:
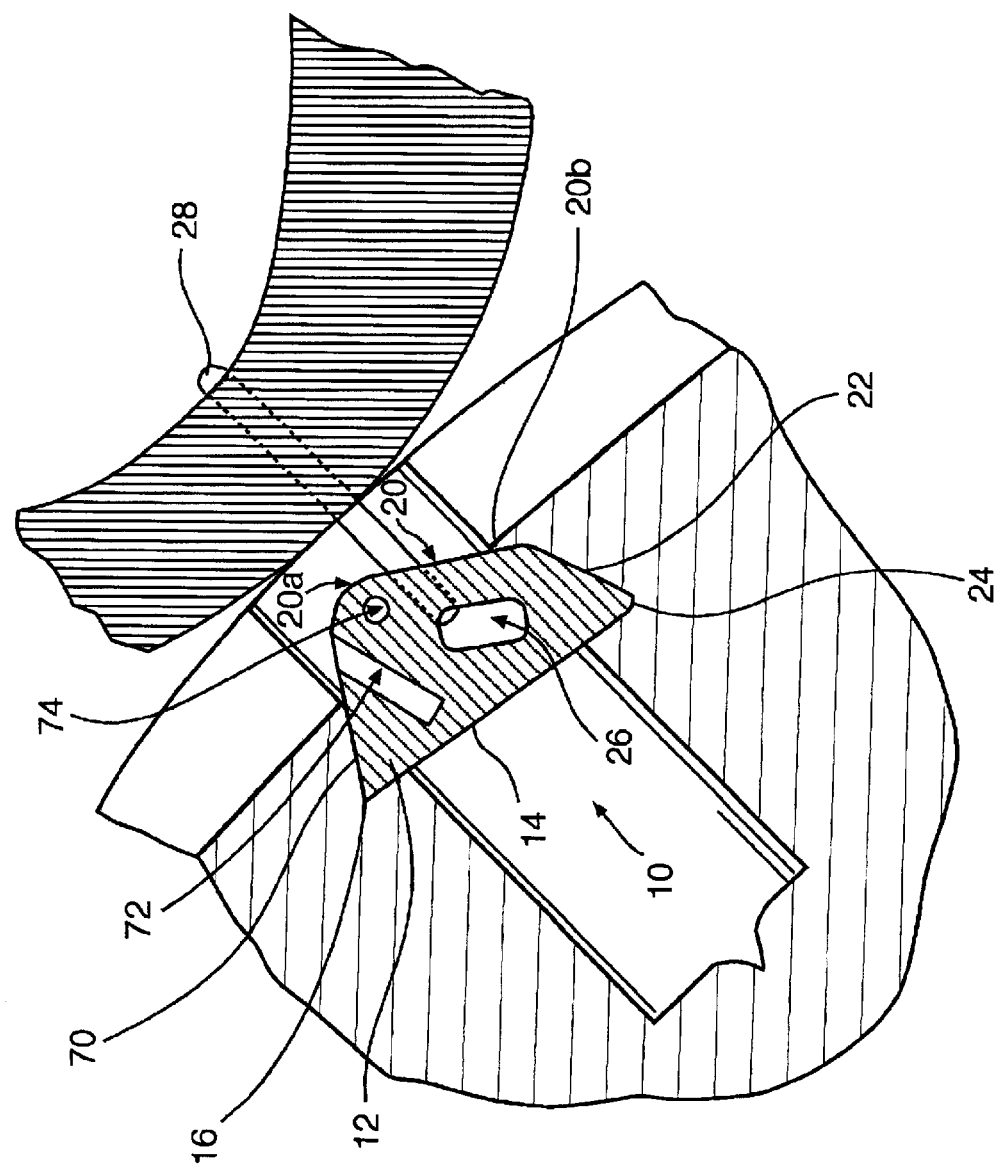
FIG. 11 is a cross-sectional view of bodily tissue being attached to the bone by a suture anchored within the bone by a suture anchor in accordance with one embodiment of the present invention.

As previously discussed, the tether 76 and/or the knot 78 are preferably configured to have a breaking strength, otherwise referred to herein as the separation force required to separate the insertion tool 50 from the suture anchor 10, of no less than the seating force for the suture anchor 10. In some instances, the separation force may be slightly greater than the seating force, but less than the pullout strength of the suture anchor 10 itself, such that the suture anchor 10 can be checked for proper seating by repeated applications of the seating force before the tether 76 is broken and the insertion tool 50 removed from the suture anchor 10. Accordingly, once the suture anchor 10 is seated, the insertion tool 50 may be removed from the inserter bore 72 by exerting a force at least as great as the required separation force so as to break the tether 76 or the knot 78, as shown in FIG. 10. FIG. 10A further illustrates the removal of the insertion tool 50, from a suture anchor 10 as shown in FIG. 1, wherein a force at least as great as the required breaking strength of the frangible portion 30a is applied to the insertion tool 50 outwardly of the bore. Accordingly, the separator extension 30 is broken and separated from the suture anchor 10 at the frangible portion 30a when the force on the insertion tool 50 exceeds the breaking strength. Once the suture anchor 10 has been implanted, the suture 28 engaged therewith through the suture bore 26 allows adjacent bodily tissue to be affixed to the bone, as shown in FIG. 11.

Thus, embodiments of the present invention provide a suture anchor system having the desirable suture anchor implantation characteristics of a flexible insertion tool comprised of a shape memory material, while allowing a predetermined seating force to be applied on the suture anchor, by the insertion tool engaged therewith, before the insertion tool is removed from the suture anchor following insertion thereof in the bore, thereby providing predetermined and consistent seating characteristics of the suture anchor in the bone.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A suture anchor system configured so as to facilitate implantation of a suture anchor within a bore formed in a bone, the bore having a wall, so as to secure a suture to the bone, said system comprising:

a suture anchor adapted to have the suture operably engaged therewith, the suture anchor having a leading edge and a trailing edge;

an insertion tool having a tip and defining a first axis, the insertion tool being discrete with respect to the suture anchor and adapted so as to be capable of implanting the suture anchor within the bore such that the suture anchor is secured in the bone, the tip being engagable with the suture anchor and being configured to cooperate therewith so as to prevent the suture anchor from rotating about the first axis, the insertion tool being configured with respect to the suture anchor such that a force exerted on the insertion tool about a second axis, the second axis being perpendicularly disposed with respect to the first axis, is capable of rotating the suture anchor about the second axis such that the leading and trailing edges initially penetrate the bore wall, and a predetermined axial seating force applied to the insertion tool, outwardly of the bore and independently of the suture, is capable of causing the leading and trailing edges to further advance within the bore wall, in excess of the initial penetration, to thereby seat the suture anchor in the bore, the insertion tool further being configured so as to require an axial separation force to be applied thereto so as to separate the insertion tool from the suture anchor, the separation force being no less than the seating force.

2. A system according to claim 1 wherein the suture anchor is comprised of at least one of a biocompatible material and a bioabsorbable material.

3. A system according to claim 1 wherein the suture anchor is comprised of at least one of polylactic acid, polydioxanone, and polyglycolic acid.

4. A system according to claim 1 wherein at least the tip of the insertion tool is comprised of a shape memory metal.

5. A system according to claim 1 wherein at least the tip of the insertion tool is comprised of a nickel-titanium alloy.

6. A system according to claim 1 wherein the suture anchor further comprises a bore for receiving the tip of the insertion tool and the insertion tool is secured to the insertion tool by a tether operably engaged therebetween, the tether being configured so as to break at no less than the seating force.

7. A system according to claim 1 wherein the suture anchor further comprises a separator extension in communication with the suture anchor through a frangible portion therebetween, the separator extension being configured to receive the tip of the insertion tool so as to engage the tip with the suture anchor, the frangible portion being configured to break at no less than the seating force.

8. A system according to claim 1 wherein the suture anchor defines a bore having a non-circular cross section, the bore being configured to receive the tip of the insertion tool, the tip having a non-circular cross-section corresponding to the bore, the tip thereby being capable or cooperating with the bore so as to prevent the suture anchor from rotating about the first axis.

9. A suture anchor system configured so as to facilitate implantation of a suture anchor within a bore formed in a bone so as to secure a suture to the bone, said system comprising:

a suture anchor adapted to have the suture operably engaged therewith;

an insertion tool having a tip and defining a first axis, the insertion tool being discrete with respect to the suture anchor and adapted so as to be capable of implanting the suture anchor within the bore such that the suture anchor is secured in the bone, the tip being separably engaged with the suture anchor and cooperating therewith so as to prevent the suture anchor from rotating about the first axis, the insertion tool being configured with respect to the suture anchor such that a rotational force exerted on the insertion tool is capable of rotating the suture anchor about a second axis, the second axis being perpendicularly disposed with respect to the first axis; and a tether operably engaged between the suture anchor and the insertion tool so as to allow a predetermined axial seating force to be applied to the insertion tool, outwardly of the bore, to seat the suture anchor in the bore, the tether being discrete with respect to the suture and being configured so as to require an axial separation force to be applied thereto in order to break the tether and separate the insertion tool from the suture anchor, the separation force being no less than the seating force.

10. A system according to claim 9 wherein the suture anchor is comprised of at least one of a biocompatible material and a bioabsorbable material.

11. A system according to claim 9 wherein the suture anchor is comprised of at lout one of polylactic acid, polydioxanone, and polyglycolic acid.

12. A system according to claim 9 wherein at least the tip of the insertion tool is comprised of a shape memory metal.

13. A system according to claim 9 wherein at least the tip of the insertion tool is comprised of a nickel-titanium alloy.

14. A system according to claim 9 wherein the suture anchor defines a bore having a non-circular cross section, the bore being configured to receive the tip of the insertion tool, the tip having a non-circular cross-section corresponding to the bare, the tip thereby being capable of cooperating with the bare so as to prevent the suture anchor from rotating about the first axis.

15. A system according to claim 9 wherein the suture anchor further defines an auxiliary bore configured to receive the tether therethrough.

16. A system according to claim 9 wherein a least one of the insertion tool and the tip is configured so as to allow the tether to be secured thereto.

17. A system according to claim 9 wherein the tether is configured as a loop extending through a bore defined by the suture anchor and through a bore defined by the insertion tool, the loop comprising a knot configured to break at no less than the seating force.

18. A system according to claim 17 wherein the bore defined by the suture anchor is configured so as to facilitate removal of the broken tether following removal of the insertion tool from the suture anchor.

19. A system according to claim 9 wherein the tether comprises a suture.

20. A method of implanting a suture anchor in a bore in a bone, the bore having a wall and the suture anchor having a leading edge, a trailing edge, and a suture operably engaged therewith, so as to secure the suture to the bone, said method comprising:

inserting the suture anchor into the bore with a discrete insertion tool having a tip and defining a first axis, the tip being engaged with the suture anchor and cooperating therewith so as to prevent the suture anchor from rotating about the first axis;

exerting a force on the insertion tool about a second axis, the second axis being perpendicularly disposed with respect to the first axis, so as to rotate the suture anchor about the second axis such that the leading and trailing edges initially penetrate the bore wall;

exerting an axial seating force on the insertion tool, outwardly of the bore, so as to cause the leading and trailing edges to further advance within the bore wall, in excess of the initial penetration, to thereby seat the suture anchor in the bore; and separating the insertion tool from the suture anchor by exerting an axial separation force on the insertion tool, the separation force being no less than the seating force.

21. A method according to claim 20 wherein inserting the suture anchor into the bore further comprises elastically deforming at least the tip of the insertion tool, externally to the suture anchor, while inserting the suture anchor into the bore.

22. A method according to claim 20 further comprising exerting an axial force on the suture, outwardly of the bore, so as to facilitate seating of the suture anchor in the bore.

23. A method of implanting a suture anchor in a bore in a bone, the suture anchor having a suture operably engaged therewith, so as to secure the suture to the bone, said method comprising:

inserting the suture anchor into the bore with a discrete insertion tool, having a tip and defining a first axis, the tip being engaged with the suture anchor and cooperating therewith so as to prevent the suture anchor from rotating about the first axis of the insertion tool, the insertion tool and the suture anchor further being operably engaged by a tether extending therebetween, the tether being discrete with respect to the suture;

exerting a rotational force on the insertion tool so as to rotate the insertion tool about a second axis, the second axis being perpendicularly disposed with respect to the first axis;

exerting an axial seating force on the insertion tool, outwardly of the bore, so as to seat the suture anchor in the bore; and separating the insertion tool from the suture anchor by exerting an axial separation force on the insertion tool so as to break the tether, the separation force being no less than the seating force.

24. A method according to claim 23 wherein inserting the suture anchor into the bore further comprises elastically deforming at least the tip of the insertion tool, externally to the suture anchor, while inserting the suture anchor into the bore.

25. A method according to claim 23 further comprising exerting an axial force on the suture, outwardly of the bore, so as to facilitate seating of the suture anchor in the bore.

26. A method according to claim 23 wherein the tether is configured as a loop comprising a knot and extending through a bore defined by the suture anchor and through a bore defined by the insertion tool, and separating the insertion tool from the suture anchor further comprises separating the insertion tool from the suture anchor by exerting an axial separation force on the insertion tool so as to break the knot.

27. A method according to claim 23 further comprising removing the broken tether from the suture anchor after separating the insertion toot from the suture anchor.

* * * * *

UNITED STATES PATENT AND TRADEMARK OFFICE
CERTIFICATE OF CORRECTION

PATENT NO.      : 6,843,799 B2
DATED           : January 18, 2005
INVENTOR(S)     : Bartlett It is certified that error appears in the above-identified patent and that said Letters Patent is hereby corrected as shown below:

Column 13,
Line 20, "lout" should read -- least --;
Lines 30 and 31, "bare" should read -- bore --.

Signed and Sealed this

Twelfth Day of April, 2005

JON W. DUDAS
*Director of the United States Patent and Trademark Office*